United States Patent [19]
Sohn et al.

[11] Patent Number: 5,665,343
[45] Date of Patent: Sep. 9, 1997

[54] POLYMERIC PLATINUM COMPLEX, PREPARATION THEREOF, AND ANTICANCER AGENT COMPRISING THEREOF

[75] Inventors: Youn Soo Sohn; Hyounggee Baek; Yang Ha Cho; Ok-Sang Jung, all of Seoul, Rep. of Korea

[73] Assignees: Il-Yang Pharm. Co., Ltd; Korea Institute of Science and Technology, both of Seoul, Rep. of Korea

[21] Appl. No.: 582,557

[22] Filed: Jan. 2, 1996

[30] Foreign Application Priority Data

Oct. 2, 1995 [KR] Rep. of Korea ................ 33694/1995

[51] Int. Cl.$^6$ ................ A61K 31/785; A61K 33/24
[52] U.S. Cl. ................ 424/78.26; 525/538; 424/649
[58] Field of Search ................ 424/78.08, 78.37, 424/649; 525/568

[56] References Cited

U.S. PATENT DOCUMENTS

| | | | |
|---|---|---|---|
| 4,151,185 | 4/1979 | Allock | 260/429 R |
| 4,931,553 | 6/1990 | Gill et al. | 536/121 |

OTHER PUBLICATIONS

Chem. A.G. 124:118193 Hyoungee et al.
M. J. Cleare, et al. "Anti–tumour platinum complexes", *Biochimie* 60, 835–850 (1978).
Evan B. Douple, *Pharmac. Ther.*, "CIS–Diamminedichloroplatinum(II): Effects of a Representative Metal Coordination Complex on Mammalian Cells" 25, 297–326 (1984).
Suzanne E. Sherman, et al. *Chem. Rev.*, "Structural Aspects of Platinum Anticancer Drug Interactions with DNA" 87, 1153–1181 (1987).
R. C. Harrison, et al. *Inorganica Chimica Act*, "An Efficient Route for the Preparation of Highly Soluble Platinum (II) Antitumour Agents" 46, L15–L16 (1980).
H. R. Allcock, et al. *Macromolecules* "Polymerization of Hexachlorocyclotriphosphazene" 8, No. 1, 36–42 (1975).

*Primary Examiner*—Peter F. Kulkosky
*Attorney, Agent, or Firm*—Scully, Scott, Murphy & Presser

[57] ABSTRACT

A novel polymeric platinum complex represented by the following formula (I):

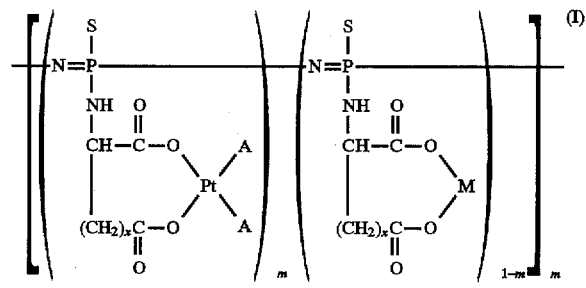

wherein, S, A, x, m and n are defined as above, a process for preparation thereof, and the use thereof as an anticancer agent.

16 Claims, No Drawings

POLYMERIC PLATINUM COMPLEX, PREPARATION THEREOF, AND ANTICANCER AGENT COMPRISING THEREOF

BACKGROUND OF THE INVENTION

The present invention relates to novel polymeric platinum complex derivatives, preparation thereof, and use thereof. More particularly, the present invention relates to controlled releasing platinum complex derivatives incorporated in polyphosphazene, preparation thereof, and use thereof as an anticancer agent.

Among the known anticancer agents, cisplatin [cis-$(NH_3)_2PtCl_2$], which was reported to exhibit high anticancer activity by Rogsenberg [B. Rosenberg, Nature 205, 698 (1965)], was approved in 1979 by FDA of the United States as an anticancer agent, and has been used as one of the most effective chemotherapeutic agents against various cancers such as testicular cancer, ovarian cancer, bladder cancer, head and neck cancer or the like. However, the use of the drug is limited because of the high toxicity [$LD_{50}$=13 mg/kg, M. J. Cleare, Biochimie 60, 835(1978)].

Meanwhile, carboplatin [cis-$(NH_3)_2$Pt(CBDCA), wherein CBDCA represents 1,1-dicyclobutanedicarboxylate], which was approved by FDA in 1989 and has been used as a second-generation anticancer agent, has much lower toxicity than that of cicplatin. However, it has lower and narrower anticancer activity as well as high price, so that it cannot be widely used either.

Therefore, extensive researches for developing a third-generation anticancer agent having higher anticancer activity and lower toxicity than those of cisplatin have been performed worldwide, but in spite of such a great deal of efforts, commercialization of a third generation anticancer drug has not been successful so far.

Requirements for the third-generation platinum anticancer agent are excellent anticancer activity comparative to or higher than that of cisplatin and low toxicity comparative to that of carboplatin as well as wide therapeutic spectrum for the cancer treatment. In addition, it should have excellent activity to cancer cells resistant to cisplatin or carboplatin, showing no cross-resistance. Furthermore, the drug should have high water solubility and chemical stability. At present, ten or more candidate compounds are in clinical studies, but no drug has been successfully commercialized.

The anticancer activity and toxicity of the cisplatin analogs have not yet been clearly verified, but the research reports on this matter up to the present may be summarized as follows:

According to Pharmac. Ther. 25, 297 (1984) and Chem. Rev. 87, 1153 (1987), cisplatin administered into blood via intravenous injection or the like, exists mostly as neutral molecules without ionization because of the high chloride ion concentration (about 100 mM) in the blood plasma and easily diffuse through cell membrane. However, since the chloride ion concentration inside the cell is low (4 mM), the cisplatin molecules diffused into the cell are subjected to hydrolysis resulting in dissociation of chloride ions, amine-platinum cations thus formed are combined with DNA in the cell mostly via intrastrand cross-linking mode to inhibit the replication of DNA, whereby kill the cell. Like other anticancer drugs, platinum complex cannot distinguish cancer cells from the normal cells, leading to cytotoxicity. The oligomers produced by hydrolysis of cisplatin are also understood to cause various toxicities in body. However, concrete relationship between the molecular structures of the neutral amine ligand and the anionic leaving group of cisplatin molecule and the anticancer activity or toxicity in body has not yet been clarified.

SUMMARY OF THE INVENTION

The present inventors have intensively studied to develop a novel third-generation platinum anticancer agent having higher anticancer activity and lower toxicity than those of the conventional cisplatin, and, as a result, found that a polymeric platinum complex represented by the following formula (I), prepared by incorporating a solubilizing group and a dicarboxylic amino acid derivative in the polyphosphazene back-bone, a biodegradable inorganic polymer, and by combining diamineplatinum(II) moiety to the dicarboxylic amino acid, shows not only much higher anticancer activity than that of cisplatin and low toxicity comparable to carboplatin, but also excellent anticancer activity to cancer cells resistant to cisplatin and to the cells of lung cancer, gastric cancer or intestine cancer which cannot be well treated by conventional cisplatin. It is presumed that, when the drug of the present invention is administered to body, the bioactive diamineplatinum(II) moiety incorporated in the polyphosphazene back-bone is controlled-releasing from the polymer chain so as to maintain an optimal efficacious level of the active moiety in the blood for certain time, so that the drug can show low toxicity and excellent anticancer activity.

More specifically, the present invention relates to a novel platinum complex incorporated in polyphosphazene, represented by the following formula (I) which has excellent anticancer activity, and preparation thereof.

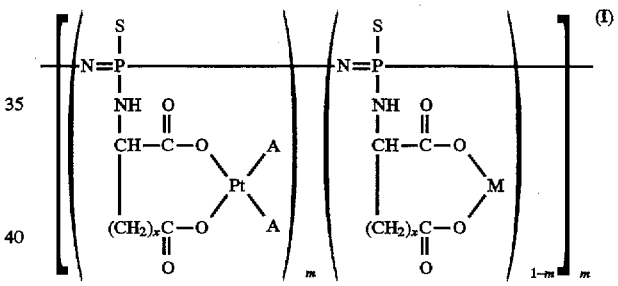

In the formula polymeric backbone is polyphosphazene having P=N repeating unit; S represents hydroxy group, alkoxy group such as methoxy, ethoxy or (2-methoxy) ethoxy group, or alkylamine group such as methylamine or dimethylamine as solubilizing group; A represents ammonia, or $C_1$–$C_3$ alkylamine such as methylamine, ethylamine or cyclopropylamine(CPA) as monodentate neutral ligand, or ʎ-type bidentate cheleting amine selected from the group consisting of ethylenediamine(en), propylenediamine(pn), 2-hydroxy-1,3-diaminopropane (HDAP), 2,2-dimethyl-1,3-diaminopropane (DMDAP), 1,1-diaminomethylcyclobutane (DAMCB), tetrahydro-4H-pyrane-4,4-dimethanamine (THPDMA), 2,2-bisaminomethyl-1,3-propandiol (BAMPDO) and trans(±)-1,2-diaminocyclohexane(DACH); x showing the type of dicarboxylic amino acid as anion group represents 0, 1 or 2, the type being aminomalonic acid (Am) derivatives when x=0, being aspartic acid derivatives (Asp) when x=1, and being glutamic acid derivatives (Glt) when x=2; M represents two alkaline metal ions such as sodium ion or potassium ion, or one alkaline earth metal ion such as calcium ion or barium ion; m showing the content of platinum complex is 0.2 to 1; and n showing degree of polymerization of polyphosphazene is 10 to 100.

The polymeric platinum complex represented by formula (I) above where a diamineplatinum(II) moiety is incorporated in the polyphosphazene back-bone is a novel compound which has never been reported, and proved to show excellent anticancer activity and superior physical properties.

A process for preparation of the platinum complex incorporated in polyphosphazene, represented by formula (I) is briefly described here-in-below.

The polymeric platinum complex represented by general formula (I) can be obtained by reacting an alkaline metal salt of general formula (I) or alkaline earth metal salt of general formula (I) obtained by incorporating a solubilizing group and a dicarboxylic amino acid derivative as a spacer group for the platinum moiety to be covalently bonded with a diamineplatinum (II) salt of general formula (IV) in a molar ratio 1:0.2 to 1:1 in an aqueous solution at room temperature.

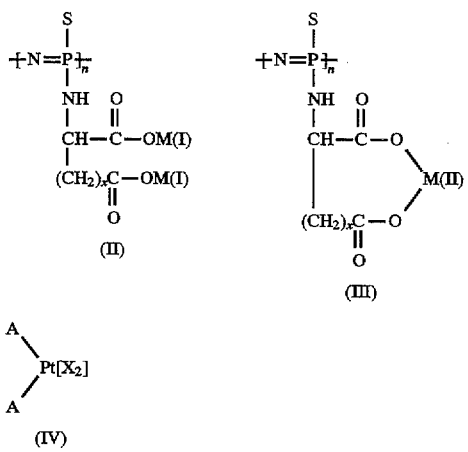

In the formula, S, A, x, m and n are defined as above, M(I) is ammonium or alkaline metal ion such as sodium or potassium ion, M(II) is alkaline earth metal ion such as barium or calcium ion, and $X_2$ is anion(s) such as two nitrate ions or one sulfate ion.

Water soluble diamineplatinum(II) salts of general formula (IV) can be prepared by reacting a diamineplatinum(II) iodide of general formula (V) and a water soluble silver salt according to a method written in the literature [R. C. Harrison, Inorg. Chimica Acta 46, L15(1980)].

A of the general formula (V) is defined as that of general formula (I). Diamineplatinum (II) iodide of general formula (V) can be easily obtained by reacting potassium tetrachloroplatinate(II) with the corresponding amine in the presence of potassium iodide according to the literature [M. J. Cleare, Biochimie 600, 835(1978)].

The process for preparation of the polymeric platinum complex derivative represented by general formula(I) according to the present invention comprises three steps: synthesis of polyphosphazene which is the main polymeric backbone to incorporate platinum complexes, incorporation of solubilizing and spacer groups into the polymeric backbone, and that incorporation of diamineplatinum(II) moiety.

At first, synthesis of polyphosphazene comprises thermal polymerization from the trimer $(N=PCl_2)_3$ to provide a linear polymer of poly(dichlorophosphazene) $(N=PCl_2)_n$ in accordance with a conventional method [e.g. Macromolecule, 8, 36(1975)]. The resultant polymer is dissolved in a solvent such as dry benzene, toluene, tetrahydrofuran or dioxane, and is added thereto an excess amount of triethylamine as a remover of hydrogen chloride. The resultant solution is slowly added to a solution where methyl, ethyl or benzyl ester or alkyl amide of a dicarboxylic amino acid such as aminomalonic acid, aspartic acid or glutamic acid, is dissolved in the same solvent in the same molar ratio as the polymer unit, and the resultant reaction mixture is stirred at room temperature. After filtering triethylamine hydrochloride precipitated, water, water soluble alcohol such as methanol, ethanol or (2-methoxy)ethanol, or water soluble amine such as methylene or dimethylamine as a solubilizing group is added together with equimolar triethylamine to the filtrate, which is further stirred for 2–10 hours, and, if required, refluxed. The resultant reaction mixture is poured into an excess amount of n-hexane, where most of the polymer is precipitated. The purification process comprising of dissolving the precipitated polymer obtained by filtering the hexane solution in a polar solvent such as tetrahydrofuran or dioxane, and pouring the solution into water to produce precipitate is repeated 2–3 times. The purified polymer is dissolved in a cosolvent of alcohol-tetrahydrofuran, and alkaline metal (Na or K) hydroxide, or alkaline earth metal (Ca or Ba) hydroxide corresponding to 1.0–1.5 equivalent to the substituted amino acid is dissolved therein. The solution mixture is stirred at room temperature for 2–10 hours for hydrolysis yielding a water soluble amino acid metal salt as precipitate. After filtering, thoroughly washing with alcohol or acetone, and drying, the precipitate is reacted with a diamineplatinum(II) intermediate as follows:

An aqueous solution of potassium tetrachloroplatinate(II) is reacted with an excess amount of potassium iodide, and then two equivalents of a desired amine(A) in an aqueous solution is added thereto to obtain diamineplatinum(II) iodide according to the method in the literature. A water soluble silver salt, e.g. silver nitrate or silver sulfate, is reacted with an equimolar diamineplatinum(II) iodide in water by stirring at room temperature for 2–10 hours. The precipitated silver iodide is filtered off to obtain water soluble diamineplatinum(II) salt of general formula(IV). The resultant aqueous solution of diamineplatinum(II) salt is finally reacted with an aqueous solution of the alkaline metal salt of amino acid incorporated in polyphosphazene of general formula (II) or that of alkaline earth metal salt of general formula(III) in a molar ratio of 0.2:1 to 1:1 to obtain diamineplatinum(II) complex of polyphosphazene of general formula (I). In order to remove the byproduct, that is, alkaline or alkaline earth metal nitrate or sulfate, thus obtained, the reaction mixture is placed in a semipermeable membrane (m.w.cutoff: 1000) vessel and dialyzed with distilled water for 10–24 hours. Alternatively, the by-product may be separated using the difference of solubility between the polyphosphazene platinum complex and the alkali metal or alkaline earth metal nitrate or sulfate. For example, where an alkaline earth metal salt of amino acid incorporated in polyphosphazene is reacted with diamineplatinum(II) sulfate, separation is performed by filtration of the alkaline earth metal sulfate which is insoluble in water. When an alkaline metal salt of amino acid incorporated in polyphosphazene is reacted with dimeplatinum(II) nitrate, potassium nitrate or sodium nitrate is produced as by-product which is very soluble in water so that it coexists with the platinum complex of polyphohphazene in the reaction mixture. However, as sodium nitrate or potassium nitrate is soluble in alcohol whereas platinum complex is hardly soluble, it can be separated using a solvent pair of water and alcohol. When sodium or potassium salt of amino acid incorporated in polyphosphazene is reacted with diamineplatinum(II) sulfate, the by-product, sodium sulfate or potassium sulfate which is water-soluble may be easily separated by the use of a solvent pair of water and acetone. The process for the preparation of the polymeric platinum complex of general formula (I) is illustrated by the scheme below:

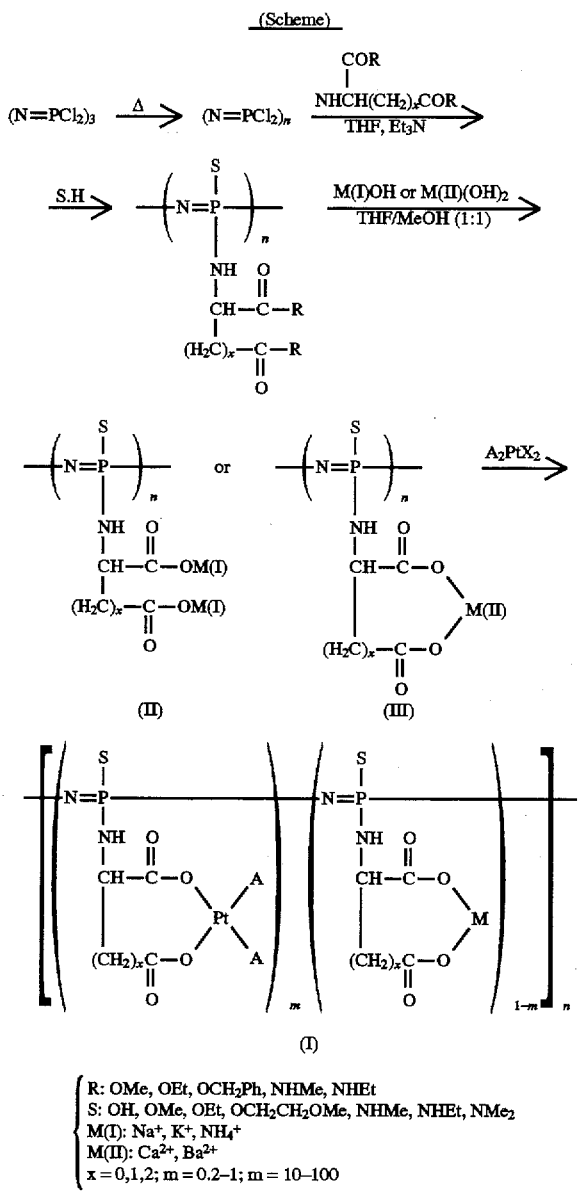

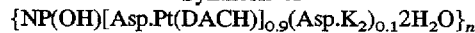

BEST MODES FOR CARRYING OUT THE INVENTION

Now, the present invention is further described by referring to the following examples. However, the present invention should not be understood to be limited to the examples.

EXAMPLE 1

Synthesis of
{NP(OH)[Asp.Pt(DACH)]$_{0.9}$(Asp.K$_2$)$_{0.1}$2H$_2$O}$_n$

Three(3.0) grams (8.63 mmol) of hexachlorocyclotriphosphazene [(NPCl$_2$)$_3$] and 0.15 g (2.25 mmol) of anhydrous aluminum chloride were introduced to a 220 mm×23 mm Pyrex ampoule. After sealing the ampoule, thermal polymerization reaction was performed at 250° C. for 2 hours with rotating the ampoule at 1 rpm to produce poly (dichlomphosphazene). The ampoule was cooled to room temperature and opened in a dry box under argon atmosphere. A solution obtained by dissolving the content in purified dry THF or benzene was directly used in the next substitution reaction.

L-Aspartoyl dibenzyl ester-p-toluenesulfonate(13.2 g, 27.2 mmol) was dissolved in 400 ml of THF, and the mixture was cooled to 0° C. Triethylamine(7.56 ml, 54.4 mmol) was added thereto and the resultant mixture was stirred for 30 minutes. A THF solution(150 ml) containing 3.0 g of poly (dichlorophosphazene) prepared above was added dropwise thereto over 1 hour, and the resultant mixture was stirred at room temperature for 20 hours. After the precipitates produced (Et$_3$N.HCl and trimethylammonium p-toluenesulfonate) were filtered off, triethylamine(3.78 ml, 27.2 mmol) and water(0.49 ml, 27.2 mmol) were added to the filtrate, and the resultant mixture was stirred at room temperature for 12 hours. The precipitate produced (Et$_3$N.HCl) was filtered off again, and the product obtained by distillation of the filtrate under reduced pressure at 30° C. was dissolved again in THF. The THF solution was added dropwise to an excess amount of n-hexane yielding a white precipitate. The precipitate was dissolved again in THF, and the solution was added dropwise to an excess amount of water to obtain a white polymer [NP(OH)(Asp.CH$_2$Ph)$_2$]$_n$, which was filtered and dried under reduced pressure(yield: 85%).

To a solution of the above polyphosphazene(4.0 g, 10.7 mmol) derivative dissolved in 80 ml of a THF-MeOH(1:1, vol %) mixed solvent KOH(1.80 g, 32.1 mmol) or NaOH (1.28 g, 32.1 mmol) in 50 ml of the same mixed solvent was added slowly and the reaction mixture was stirred for 5 hours. The resultant precipitate was filtered and washed with a sufficient amount of the THF-MeOH mixed solvent and ethyl ether. This was dissolved in 40 ml of 2N KOH or 2N NaOH aqueous solution, and the solution was added dropwise to 500 ml of THF-MeOH(1:1,vol %) mixed solvent. The precipitate [NP(OH)(Asp.K$_2$)] or [NP(OH)(Asp.Na$_2$)]$_n$ thus obtained by hydrolysis was filtered and washed with methanol and ethyl ether, and then, dried under vacuum (yield: 90%).

Meanwhile, platinum intermediate (DACH)PtI$_2$(2.08 g, 3.70 mmol) and Ag$_2$SO$_4$(1.15 g, 3.70 mmol) were reacted in 100 ml of water at room temperature for 10 hours and the precipitated AgI was filtered off. The filtrate containing (DACH)PtSO$_4$ was added to 30 ml of aqueous solution of [NP(OH)(Asp.K$_2$)]$_n$ (1.0 g, 3.70 mmol) prepared above and the resultant reaction mixture was stirred for 1 hour under darkness. To remove the byproduct K$_2$SO$_4$, the reaction mixture was condensed to 30 ml under reduced pressure, and then acetone (400 ml) was added thereto. The precipitated solid product was filtered and washed with ethyl ether and then, dried under reduced pressure to obtain the desired polymeric platinum complex.

Elemental Analysis (%):
C, 22.3; H, 4.27; N, 9.58; P, 5.25; Pt, 34.3
Calculated (%): C, 21.6; H, 4.50; N, 10.1; P, 5.58; Pt, 35.2
$^1$H NMR(D$_2$O, ppm): 1.2–1.3(4H), 1.6(2H), 2.1(2H), 2.4(2H), 2.7(2H), 3.8(1H)
IR (KBr cell, cm$^{-1}$): 516(m), 714(m), 816(m), 1034(m), 1065(m), 1172(m), 1248(m), 1384(s), 1450(m), 1618(s), 3213(s), 3428(s).

EXAMPLE 2

Synthesis of {NP(OH)[Asp.Pt(DACH)]$_{0.5}$(Asp.K$_2$)$_{0.5}$·3H$_2$O}$_n$ (DACH)PtI$_2$(1.04 g, 1.85 mmol), Ag$_2$SO$_4$(0.58 g, 1.85 mmol) and [NP(OH)(Asp.K$_2$)]$_n$ (1.0 g, 3.70 mmol) were reacted in accordance with the same procedure as Example 1 to obtain the title complex.

Elemental Analysis (%): C, 18.5; H, 3.31; N, 5.86; P, 6.56; Pt, 21.4.

Calculated (%):

C, 19.1; H, 3.87; N, 6.37; P, 7.05; Pt, 22.2.

$^1$H NMR(D$_2$O, ppm): 1.2–1.3(4H), 1.6(2H), 2.1(2H), 2.4(2H), 2.7(2H), 3.8(1H).

IR (KBr cell, cm$^{-1}$): 518(m), 614(m), 1065(m), 1119(s), 1167(m), 1307(m), 1393(s), 1591(s), 1645(m), 2934(m), 3213(s), 3406(s).

EXAMPLE 3

Synthesis of {NP(OH)[Asp.Pt(DACH)]$_{0.2}$(Asp.K$_2$)$_{0.8}$·3H$_2$O}$_n$ (DACH)PtI$_2$(0.42 g, 0.74 mmol), Ag$_2$SO$_4$(0.23 g, 0.74 mmol) and [NP(OH)(Asp.K$_2$)]$_n$ (1.0 g, 3.70 mmol) were reacted in accordance with the same procedure as Example 1 to obtain the title complex.

Elemental Analysis (%): C, 15.9; H, 3.14; N, 8.25; P, 7.38; Pt, 9.77.

Calculated (%): C, 16.9; H, 3.76; N, 9.08; P, 8.36; Pt, 10.54.

$^1$H NMR(D$_2$O, ppm): 1.2–1.3(4H), 1.6(2H), 2.1(2H), 2.4(2H), 2.7(2H), 3.8(1H).

IR (KBr cell, cm$^{-1}$): 534(m), 620(m), 979(m), 1060(m), 1124(s), 1205(m), 1307(m), 1404(s), 1591(s), 2945(m), 3224(s), 3406(s).

EXAMPLE 4

Synthesis of {NP(OH)[Asp.Pt(CPA)$_2$]$_{0.9}$(Asp.K$_2$)$_{0.1}$·2H$_2$O}$_n$ (CPA)$_2$PtI$_2$(2.08 g, 3.70 mmol), Ag$_2$SO$_4$(1.15 g, 3.70 mmol) and [NP(OH)(Asp.K$_2$)]$_n$ (1.0 g, 3.70 mmol) were reacted in accordance with the same procedure as Example 1 to obtain the title complex.

Elemental Analysis (%): C, 21.7; H, 3.82; N, 9.33; P, 5.18; Pt, 34.7.

Calculated (%): C, 21.9; H, 4.23; N, 10.35; P, 6.02; Pt, 34.1.

$^1$H NMR(D$_2$O, ppm): 0.7(8H), 2.5(2H), 3.7(1H).

IR (KBr cell, cm$^{-1}$): 619(m), 827(m), 964(m), 1030(m), 1122(m), 1261(m), 1375(s), 1637(s), 3103(m), 3188(s), 3404(m).

EXAMPLE 5

Synthesis of {NP(OH)[Asp.Pt(NH$_3$)$_2$]·3H$_2$O}$_n$ (NH$_3$)$_2$PtI$_2$(1.79 g, 3.70 mmol), Ag$_2$SO$_4$(1.15 g, 3.70 mmol) and [NP(OH)(L-Asp.K$_2$)]$_n$ (1.0 g, 3.70 mmol) were reacted in accordance with the same procedure as Example 1 to obtain the title complex.

Elemental Analysis (%): C, 10.4; H, 2.88; N, 9.54; P, 5.98; Pt, 40.4

Calculated (%): C, 10.1; H, 3.37; N, 8.84; P, 6.52; Pt, 41.1

$^1$H NMR(D$_2$O, ppm): 2.7(2H), 3.9(1H)

IR (KBr cell, cm$^{-1}$): 619(m), 1118(m), 1369(m), 1639(s), 3128(m), 3259(s), 3443(m)

EXAMPLE 6

Synthesis of {NP(OH)[Asp.Pt(en)]$_{0.85}$(Asp.K$_2$)$_{0.15}$·2H$_2$O}$_n$ (en)PtI$_2$(1.88 g, 3.70 mmol), Ag$_2$SO$_4$(1.15 g, 3.70 mmol) and [NP(OH)(L-Asp.K$_2$)]$_n$ (1.0 g, 3.70 mmol) were reacted in accordance with the same procedure as Example 1 to obtain the title complex.

Elemental Analysis (%): C, 15.8; H, 4.54; N, 10.7; P, 6.11; Pt, 36.4

Calculated (%): C, 15.0; H, 3.55; N, 11.4; P, 6.78; Pt, 36.3

$^1$H NMR(D$_2$O, ppm): 2.4–2.6(6H), 3.8(1H)

IR (KBr cell, cm$^{-1}$): 570(m), 765(m), 1049(m), 1128(m), 1291(m), 1400(s), 1638(s), 3267(m), 3450(m)

EXAMPLE 7

Synthesis of {NP(OH)[Asp.Pt(pn)]$_{0.85}$(Asp.K$_2$)$_{0.15}$·2H$_2$O}$_n$ (pn)PtI$_2$(1.94 g, 3.70 mmol), Ag$_2$SO$_4$(1.15 g, 3.70 mmol) and [NP(OH)(L-Asp.K$_2$)]$_n$ (1.0 g, 3.70 mmol) were reacted in accordance with the same procedure as Example 1 to obtain the title complex.

Elemental Analysis (%): C, 16.5; H, 4.43; N, 10.7; P, 6.14; Pt, 35.4

Calculated (%): C, 16.7; H, 3.81; N, 11.0; P, 6.58; Pt, 35.2

$^1$H NMR(D$_2$O, ppm): 1.4(2H), 2.4–2.7(6H), 3.8(1H)

IR (KBr cell, cm$^{-1}$): 530(m), 936(m), 1108(m), 1196(m), 1291(m), 1402(s), 1634(s), 2932(m), 3224(m), 3428(m)

EXAMPLE 8

Synthesis of {NP(OH)[Asp.Pt(NH$_2$CH$_3$)$_2$]$_{0.85}$(Asp.K$_2$)$_{0.15}$·2H$_2$O}$_n$ (CH$_3$NH$_2$)$_2$PtI$_2$(1.89 g, 3.70 mmol), Ag$_2$SO$_4$(1.15 g, 3.70 mmol) and [NP(OH)(L-Asp.K$_2$)]$_n$ (1.0 g, 3.70 mmol) were reacted in accordance with the same procedure as Example 1 to obtain the title complex.

Elemental Analysis (%): C, 15.1; H, 4.58; N, 10.8; P, 6.36; Pt, 36.5

Calculated (%): C, 14.9; H, 3.91; N, 11.3; P, 6.76; Pt, 36.2

$^1$H NMR(D$_2$O, ppm): 2.4–2.7(8H), 3.8(1H)

IR (KBr cell, cm$^{-1}$): 582(m), 753(m), 1084(m), 1237(m), 1418(s), 1621(s), 2923(m), 3218(m), 3421(m)

EXAMPLE 9

Synthesis of {NP(OH)[Asp.Pt(NH$_2$C$_2$H$_5$)$_2$]$_{0.8}$(Asp.K$_2$)$_{0.2}$·2H$_2$O}$_n$ (NH$_2$C$_2$H$_5$)$_2$PtI$_2$(1.99 g, 3.70 mmol), Ag$_2$SO$_4$(1.15 g, 3.70 mmol) and [NP(OH)(L-Asp.K$_2$)]$_n$ (1.0 g, 3.70 mmol) were reacted in accordance with the same procedure as Example 1 to obtain the title complex.

Elemental Analysis (%): C, 18.3; H, 4.32; N, 10.8; P, 6.20; Pt, 33.6

Calculated (%): C, 18.3; H, 4.40; N, 10.7; P, 6.56; Pt, 33.1

$^1$H NMR(D$_2$O, ppm): 1.1(6H), 2.5–2.8(6H), 3.8(1H)

IR (KBr cell, cm$^{-1}$): 603(m), 762(m), 1064(m), 1201(m), 1231(m), 1407(s), 1633(s), 2934(m), 3214(s), 3402(s)

EXAMPLE 10

Synthesis of {NP(OH)[Asp.Pt(HDAP)]$_{0.8}$(Asp.K$_2$)$_{0.2}$·2H$_2$O}$_n$ (HDAP)PtI$_2$(1.99 g, 3.70 mmol), Ag$_2$SO$_4$ (1.15 g, 3.70 mmol) and [NP(OH)(L-Asp.K$_2$)]$_n$ (1.0 g, 3.70 mmol) were reacted in accordance with the same procedure as Example 1 to obtain the title complex.

Elemental Analysis (%): C, 15.9; H, 4.42; N, 10.2; P, 6.13; Pt, 33.1

Calculated (%): C, 16.3; H, 3.20; N, 10.7; P, 6.56; Pt, 33.1

$^1$H NMR(D$_2$O, ppm): 2.3–2.5(6H), 3.8(1H)

IR (KBr cell, cm$^{-1}$): 532(m), 851(m), 974(m), 1071(m), 1189(m), 1312(m), 1402(s), 1632(s), 3202(m), 3449(m)

EXAMPLE 11

Synthesis of {NP(OH)[Asp.Pt(DMDAP)]$_{0.8}$(Asp.K$_2$)$_{0.2}$·2H$_2$O}$_n$ (DMDAP)PtI$_2$(2.04 g, 3.70 mmol), Ag$_2$SO$_4$(1.15 g, 3.70 mmol) and [NP(OH)(L-Asp.K$_2$)]$_n$ (1.0 g, 3.70 mmol) were reacted in accordance with the same procedure as Example 1 to obtain the title complex.

Elemental Analysis (%): C, 21.4; H, 5.26; N, 9.52; P, 6.23; Pt, 32.8

Calculated (%): C, 20.0; H, 4.31; N, 10.5; P, 6.43; Pt, 32.4

$^1$H NMR(D$_2$O, ppm): 1.4(6H), 2.3–2.5(6H), 3.8(1H)

IR (KBr cell, cm$^{-1}$): 522(m), 700(m), 915(m), 1108(m), 1200(m), 1221(m), 1307(m), 1400(m), 1632(s), 2945(m), 3224(s), 3442(s)

EXAMPLE 12

Synthesis of {NP(OH)[Asp.Pt(DAMCB)]$_{0.8}$(Asp.K$_2$)$_{0.2}$·2H$_2$O}$_n$ (DAMCB)PtI$_2$(2.08 g, 3.70 mmol), Ag$_2$SO$_4$(1.15 g, 3.70 mmol) and [NP(OH)(L-Asp.K$_2$)]$_n$ (1.0 g, 3.70 mmol) were reacted in accordance with the same procedure as Example 1 to obtain the title complex.

Elemental Analysis (%): C, 22.1; H, 4.51; N, 9.84; P, 5.87; Pt, 32.1

Calculated (%): C, 21.5; H, 4.23; N, 10.3; P, 6.31; Pt, 31.8

$^1$H NMR(D$_2$O, ppm): 0.8–1.1(6H), 2.2–2.4(6H), 3.8(1H)

IR (KBr cell, cm$^{-1}$): 530(m), 920(m), 1087(m), 1114(m), 1200(m), 1400(s), 1632(s), 2966(m), 3224(m), 3442(m)

EXAMPLE 13

Synthesis of {NP(OCH$_3$)[Asp.Pt(DACH)]$_{0.8}$(Asp.K$_2$)$_{0.2}$·2H$_2$O}$_n$

L-Aspartoyl dibenzyl ester-p-toluenesulfonate (13.2 g, 27.2 mmol) was dissolved in 400 ml of THF, and the mixture was cooled to 0° C. Triethylamine(7.56 ml, 54.4 mmol) was added thereto and the resultant mixture was stirred for 30 minutes. A THF solution(150 ml) containing 3.0 g of polydichlorophosphazene prepared according to Example 1 was added dropwise thereto and the resultant mixture was stirred at room temperature for 20 hours. Precipitates formed (Et$_3$N.HCl and triethylammonium p-toluenesulfonate) were filtered off and then, the filtrate was condensed to 300 ml below 30 ° C. To the filtrate, were added methanol(50ml) and triethylamine(3.78 ml, 27.7 mmol), and the resultant mixture was stirred at 60°–70° C. for 14 hours. The precipitate formed (Et$_3$N.HCl) was filtered off, and the product obtained by evaporating the solvent of the filtrate below 30° C. was dissolved again in THF. The THF solution was added dropwise to an excess amount of n-hexane to produce a white precipitate. The precipitate was dissolved again in THF, and the solution was added dropwise to an excess mount of water to obtain a white polymer as precipitate. This procedure was repeated twice and then, the resultant polymer [NP(OCH$_3$)(AsP.(CH$_2$Ph)$_2$)]$_n$ was dried under reduced pressure. After hydrolysing the synthesized polyphosphazene derivative (4.0 g, 10.7 mmol) as in Example 1, (DACH)PtI$_2$(1.98 g, 3.52 mmol), Ag$_2$SO$_4$(1.10 g, 3.52 mmol) and [NP(OCH$_3$)(L-Asp.K$_2$)]$_n$ (1.0 g, 3.52 mmol) were reacted in accordance with the same procedure as Example 1 to obtain the polymeric platinum complex.

Elemental Analysis (%): C, 23.4; H, 4.45; N, 9.67; P, 5.88; Pt, 31.8

Calculated (%): C, 23.3; H, 4.51; N, 9.98; P, 6.13; Pt, 30.9

$^1$H NMR(D$_2$O, ppm): 1.2–1.3(4H), 1.6(2H), 2.2(2H), 2.5(2H), 2.7(2H), 3.4(3H), 3.8(1H)

IR (KBr cell, cm$^{-1}$): 516(m), 613(m), 1110(m), 1034(m), 1172(m), 1253(m), 1398(s), 1594(s), 2940(m), 3218(s), 3426(m)

EXAMPLE 14

Synthesis of {NP(OCH$_3$)[Asp.Pt(NH$_3$)$_2$]$_{0.85}$(Asp.K$_2$)$_{0.15}$·2H$_2$O}$_n$ (NH$_3$)$_2$PtI$_2$(1.78 g, 3.52 mmol), Ag$_2$SO$_4$(1.10 g, 3.52 mmol) and [NP(OCH$_3$)(Asp.K$_2$)]$_n$ (1.0 g, 3.52 mmol) were reacted in accordance with the same procedure as Example 13 to obtain the title complex.

Elemental Analysis (%): C, 13.1; H, 4.33; N, 11.0; P, 7.42; Pt, 37.1

Calculated (%): C, 13.5; H, 3.64; N, 11.6; P, 6.94; Pt, 37.2

$^1$H NMR(D$_2$O, ppm): 2.5(2H), 3.3(3H), 3.8(1H)

IR (KBr cell, cm$^{-1}$): 520(m), 714(m), 1038(m), 1174(m), 1205(m), 1377(s), 1624(s), 2927(m), 3267(s), 3442(m)

EXAMPLE 15

Synthesis of {NP(OC$_2$H$_5$)[Asp.Pt(DACH)]$_{0.8}$(Asp.K$_2$)$_{0.2}$· 2H$_2$O}$_n$ Polydichlorophosphagen(3.0g), L-aspartoyl dibenzyl ester-p-toluenesulfonate(13.2 g, 27.2 mmol), ethanol(50 ml), (DACH)PtI$_2$(1.88 g, 3.34 mmol), Ag$_2$SO$_4$(1.04 g, 3.34 mmol) and [NP(OC$_2$H$_5$)(Asp.K$_2$)]$_n$ (1.0 g, 3.34 mmol) were reacted in accordance with the same procedure as Example 13 to obtain the title complex.

Elemental Analysis (%): C, 28.7; H, 5.10; N, 9.01; P, 5.58; Pt, 29.1

Calculated (%): C, 28.6; H, 4.69; N, 9.69; P, 5.95; Pt, 30.0

$^1$H NMR(D$_2$O, ppm): 1.1–1.3(4H), 1.4–1.6(6H), 2.2(2H), 2.4(2H), 2.8(2H), 3.4(2H), 3.8(1H)

IR (KBr cell, cm$^{-1}$): 516(m), 614(m), 963(m), 1032(m), 1122(m), 1173(m), 1248(m), 1302(m), 1390(s), 1624(s), 2923(m), 3212(s), 3426(s)

EXAMPLE 16

Synthesis of {NP(OC$_2$H$_5$)[Asp.Pt(NH$_3$)$_2$]$_{0.85}$(Asp.K$_2$)$_{0.15}$·2H$_2$O}$_n$ (NH$_3$)$_2$PtI$_2$(1.61 g, 3.34 mmol), Ag$_2$SO$_4$(1.04 g, 3.34 mmol) and [NP(OC$_2$H$_5$)(Asp.K$_2$)]$_n$ (1.0 g, 3.34 mmol) were reacted in accordance with the same procedure as Example 13 to obtain the title complex.

Elemental Analysis (%): C, 19.8; H, 4.46; N, 10.9; P, 6.01; Pt, 35.8

Calculated (%): C, 20.1; H, 3.96; N, 11.2; P, 6.72; Pt, 36.0

$^1$H NMR(D$_2$O, ppm): 1.3(3H), 2.6(2H), 3.3(2H), 3.8(1H)

IR (KBr cell, cm$^{-1}$): 601(m), 889(m), 1043(m), 1218(m), 1382(s), 1630(s), 2936(m), 3213(s), 3426(s)

EXAMPLE 17

Synthesis of $\{NP(OC_2H_4OCH_3)[Asp.Pt(DACH)]_{0.8}(Asp.K_2)_{0.2}\cdot 2H_2O\}_n$ Polydichlorophosphazene(3.0 g), L-aspartoyl dibenzyl ester-p-toluenesulfonate (13.2 g, 27.2 mmol), CH$_3$OCH$_2$CH$_2$ONa (2.70 g, 27.2 mmol), (DACH)PtI$_2$(1.71 g, 3.04 mmol), Ag$_2$SO$_4$(0.95 g, 3.04 mmol) and [NP(OCH$_2$CH$_2$OCH$_3$)(Asp.K$_2$)]$_n$ (1.0 g, 3.04 mmol) were reacted in accordance with the same procedure as Example 13 to obtain the polymeric platinum complex.

Elemental Analysis (%): C, 25.7; H, 5.38; N, 8.76; P, 5.10; Pt, 28.9

Calculated (%): C, 25.8; H, 4.81; N, 9.18; P, 5.64; Pt, 28.4

$^1$H NMR(D$_2$O, ppm): 1.2–1.4(6H), 1.6(2H), 2.1(2H), 2.4(2H), 2.7(2H), 3.2–3.4(5H), 3.8(1H)

IR (KBr cell, cm$^{-1}$): 516(m), 840(m), 969(m), 1044(m), 1124(m), 1162(m), 1205(m), 1253(m), 1398(s), 1624(m), 2940(m), 3234(s), 3440(s)

EXAMPLE 18

Synthesis of $\{NP(NHCH_3)[Asp.Pt(DACH)]_{0.8}(Asp.K_2)_{0.2}\cdot 2H_2O\}_n$

L-Aspartoyl dibenzyl ester p-toluenesulfonate (13.2 g, 27.2 mmol) was dissolved in 400 ml of THF, and the mixture was cooled to 0° C. Triethylamine(7.56 ml, 54.4 mmol) was added thereto and the resultant mixture was stirred for 30 minutes. A THF solution(150 ml) containing 3.0 g, of polydichlorophosphazene prepared according to Example 1 was added dropwise thereto and the resultant mixture was stirred at room temperature for 20 hours. After filtering the precipitates produced (Et$_3$N.HCl and triethylammonium p-toluenesulfonate), the filtrate was cooled to 0° C. Methylamine(54.4 mmol, liquified using dry ice-acetone mixed coolant) was added thereto and the resultant mixture was stirred for 10 hours. The solvent of the reaction mixture was removed and the product obtained was dissolved in 50 ml of methanol. This solution was dialyzed using dialysis membrane(mw. cutoff: 1000) for 48 hours and then reduced to 30 ml. The solution was added dropwise to an excess amount of acetone to obtain a white polymer as precipitate. After hydrolysing the synthesized polyphosphazene derivative(4.0 g, 9.89 mmol) prepared above as in Example 1, (DACH)PtI$_2$(2.08 g, 3.70 mmol), Ag$_2$SO$_4$(1.15 g, 3.70 mmol) and [NP(NHCH$_3$)(Asp.K$_2$)]$_n$ (1.0 g, 3.70 mmol) were reacted in accordance with the same procedure as Example 1 to obtain the polymeric platinum complex.

Elemental Analysis (%): C, 24.8; H, 4.62; N, 12.4; P, 5.92; Pt, 30.8

Calculated (%): C, 4.3; H, 4.64; N, 12.8; P, 6.14; Pt, 31.0

$^1$H NMR(D$_2$O, ppm): 1.2–1.4(4H), 1.6(2H), 2.1(2H), 2.4–2.6(7H), 3.8(1H)

IR (KBr cell, cm$^{-1}$): 518(m), 614(m), 716(m), 904(m), 1060(m), 1114(m), 1248(m), 1307(m), 1162(m), 1387(s), 1586(s), 1645(s), 2923(m), 3245(s), 3385(s)

EXAMPLE 19

Synthesis of $\{NP(NHCH_3)[Asp.Pt(NH_3)]_{0.85}(Asp.K_2)_{0.15}\cdot 2H_2O\}_n$ (NH$_3$)$_2$PtI$_2$(1.79 g, 3.70 mmol), Ag$_2$SO$_4$(1.15 g, 3.70 mmol) and [NP(NHCH$_3$)(L-Asp.K$_2$)]$_n$ (1.0 g, 3.70 mmol) were reacted in accordance with the same procedure as Example 18 to obtain the title complex.

Elemental Analysis (%): C, 13.3; H, 4.28; N, 14.7; P, 6.89; Pt, 37.4

Calculated (%): C, 13.5; H, 3.87; N, 14.8; P, 6.96; Pt, 37.3

$^1$H NMR(D$_2$O, ppm):

2.5(3H), 2.7(2H), 3.9(1H)

IR (KBr cell, cm$^{-1}$): 518(m), 963(m), 1114(m), 1162(m), 1231(m), 1253(m), 1302(m), 1401(s), 1639(s), 2945(m), 3245(s), 3421(s)

EXAMPLE 20

Synthesis of $\{NP[N(CH_3)_2][Asp.Pt(DACH)]_{0.8}(Asp.K_2)_{0.2}\cdot 2H_2O\}_n$ Poly(dichlorophosphazene)(3.0 g), L-aspartoyl dibenzyl ester-p-toluenesulfonate(13.2 g, 27.2 mmol), dimethylamine hydrochloride(2.22 g, 27.2 mmol), (DACH)PtI$_2$(1.89 g, 3.36 mmol), Ag$_2$SO$_4$(1.05 g, 3.36 mmol) and [NP(N(CH$_3$)$_2$)(Asp.K$_2$)]$_n$ (1.0 g, 3.36 mmol) were reacted in accordance with the same procedure as Example 18 to obtain the polymeric platinum complex.

Elemental Analysis (%): C, 23.6; H, 4.98; N, 11.9; P, 5.83; Pt, 30.7

Calculated (%): C, 23.6; H, 4.90; N, 12.4; P, 5.98; Pt, 30.1

$^1$H NMR(D$_2$O, ppm): 1.1–1.3(4H), 1.5(2H), 2.1(2H), 2.3–2.5(8H), 3.9(1H)

IR (KBr cell, cm$^{-1}$): 502(m), 625(m), 985(m), 1065(m), 1151(m), 1237(m), 1291(m), 1392(s), 1632(s), 2923 (m), 3191 (s), 3442(s)

EXAMPLE 21

Synthesis of $\{NP(OH)[Glt.Pt(DACH)]_{0.9}(Glt.K_2)_{0.1}\cdot 2H_2O\}_n$

Poly(dichlorophosphazene)(3.0 g), L-glutamoyl dibenzyl ester-p-toluenesulfonate(13.6 g, 27.2 mmol), triethylamine (7.57 ml, 54.4 mmol), H$_2$O (0.49 ml, 27.2 mmol), [NP(OH)(Glt.K$_2$)]$_n$ (1.0 g, 3.52 mmol), (DACH)PtI$_2$ (1.98 g, 3.52 mmol) and Ag$_2$SO$_4$(1.10 g, 3.52 mmol) were reacted in accordance with the same procedure as Example 1 to obtain the reaction mixture containing the polymeric platinum complex, which was subjected to dialysis for 15 hours using a semipermeable membrane (m.w. cutoff:1000) to remove the byproduct K$_2$SO$_4$. The purified solution was then freeze-dried under vacuum to obtain the title complex.

Elemental Analysis (%): C, 23.6; H, 4.21; N, 9.59; P, 6.08; Pt, 34.0

Calculated (%): C, 23.6; H, 4.50; N, 10.1; P, 5.86; Pt, 33.2

$^1$H NMR(D$_2$O, ppm): 1.1–1.3(4H), 1.5(2H), 2.0(4H), 2.3(4H), 3.7(1H)

IR (KBr cell, cm$^{-1}$): 518(m), 615(m), 829(m), 1033(m), 1064(m), 1170(m), 1345(m), 1400(s), 1447(m), 1634(s), 2937(m), 3234(s), 3422(s)

EXAMPLE 22

Synthesis of $\{NP(OH)[Glt.Pt(CPA)_2]_{0.9}(Glt.K_2)_{0.1}\cdot 2H_2O\}_n$ (CPA)$_2$PtI$_2$(1.98 g, 3.52 mmol), Ag$_2$SO$_4$(1.10 g, 3.52 mmol) and [NP(OH)(Glt.K$_2$)]$_n$ (1.0 g, 3.52 mmol) were reacted in accordance with the same procedure as Example 21 to obtain the title complex.

Elemental Analysis (%): C, 24.1; H, 3.98; N, 9.10; P, 4.97; Pt, 34.0

Calculated: C, 23.6; H, 4.50; N, 10.1; P, 5.86; Pt, 33.2

$^1$H NMR(D$_2$O, ppm) 0.7(8H), 2.1–2.4(6H), 3.8(1H)

IR (KBr cell, cm$^{-1}$) 1124(m), 1388(s), 1631(s), 3086(s), 3184(s)

EXAMPLE 23

Synthesis of {NP(OH)[Glt.Pt(NH$_3$)$_2$].3H$_2$O}$_n$ (NH$_3$)$_2$PtI$_2$(1.70 g, 3.52 mmol, Ag$_2$SO$_4$(1.10 g, 3.52 mmol) and [NP(OH)(Glt.K$_2$)]$_n$ (1.0 g, 3.52 mmol) were reacted in accordance with the same procedure as Example 21 to obtain the title complex.

Elemental Analysis (%): C, 12.0; H, 3.21; N, 10.1; P, 5.83; Pt, 38.4

Calculated: C, 12.3; H, 3.88; N, 11.5; P, 6.33; Pt, 39.9

$^1$H NMR(D$_2$O, ppm) 2.2(2H), 2.5(2H), 3.8(1H)

IR (KBr cell, cm$^{-1}$) 526(m), 617(m), 857(m), 1111(m), 1344(m), 1386(s), 1628(s), 2960(m), 3092(s), 3250(s), 3460 (s)

EXAMPLE 24

Synthesis of {NP(OH)[Glt.Pt(THPDMA)]$_{0.8}$(Glt.K$_2$)$_{0.2}$.2H$_2$O}$_n$ (THPDMA)PtI$_2$ (2.09 g, 3.52 mmol), Ag$_2$SO$_4$(1.10 g, 3.52 mmol) and [NP(OH)(Glt.K$_2$)]$_n$ (1.0 g, 3.52 mmol) were reacted in accordance with the same procedure as Example 21 to obtain the polymeric platinum complex.

Elemental Analysis (%): C, 23.8; H, 4.33; N, 10.7; P, 5.45; Pt, 31.5

Calculated: C, 24.1; H, 4.53; N, 9.53; P, 5.85; Pt, 29.5

$^1$H NMR(D$_2$O, ppm) 1.5(4H), 2.4–2.6(8H), 3.7(5H)

IR (KBr cell, cm$^{-1}$) 518(m), 620(m), 1116(m), 1167(m), 1384(s), 1638(s), 2945(m), 3234(s), 3446(s)

EXAMPLE 25

Synthesis of {NP(OH)[Glt.Pt(BAMPDO)]$_{0.8}$(Glt.K$_2$)$_{0.2}$.2H$_2$O}$_n$ (BAMPDO)PtI$_2$ (2.05 g, 3.52 mmol), Ag$_2$SO$_4$(1.10 g, 3.52 mmol) and [NP(OH)(Glt.K$_2$)]$_n$ (1.0 g, 3.52 mmol) were reacted in accordance with the same procedure as Example 21 to obtain the title complex.

Elemental Analysis (%): C, 22.4; H, 5.62; N, 11.6; P, 6.12; Pt, 34.2

Calculated: C, 22.3; H, 4.61; N, 10.4; P, 6.38; Pt, 32.2

$^1$H NMR(D$_2$O, ppm) 2.0–2.6(12H), 3.6(1H)

IR (KBr cell, cm$^{-1}$) 526(m), 1044(m), 1228(m), 1275(m), 1384(s), 1457(m), 1618(s), 2925(m), 3202(s), 3404(s)

EXAMPLE 26

Synthesis of {NP(OCH$_3$)[Glt.Pt(DACH)]$_{0.8}$(Glt.K$_2$)$_{0.2}$.2H$_2$O}$_n$

Poly(dichlorophosphazene)(3.0 g), L-glutamoyl dibenzyl ester p-toluenesulfonate (13.6 g, 27.2 mmol), methanol(50 ml), (DACH)PtI$_2$ (1.89 g, 3.35 mmol), Ag$_2$SO$_4$(1.04 g, 3.35 mmol) and [NP(OCH$_3$)(Glt.K$_2$)]$_n$ (1.0 g, 3.35 mmol) were reacted in accordance with the same procedure as Example 13 to obtain the polymeric platinum complex.

Elemental Analysis (%): C, 25.0; H, 4.66; N, 9.26; P, 5.90; Pt, 29.4

Calculated: C, 25.0; H, 4.70; N, 9.71; P, 5.97; Pt, 30.1

$^1$H NMR(D$_2$O, ppm) 1.1–1.3(4H), 1.5(2H), 2.1(4H), 2.4 (4H), 3.3(3H), 3.8(1H)

IR (KBr cell, cm$^{-1}$) 514(m), 609(m), 813(m), 1052(m), 1170(m), 1213(m), 1240(m), 1387(s), 1618(s), 2940(m), 3254(s), 3420(s)

EXAMPLE 27

Synthesis of {NP(OCH$_3$)[Glt.Pt(NH$_3$)$_2$]$_{0.85}$(Glt.K$_2$)$_{0.15}$.2H$_2$O}$_n$ (NH$_3$)$_2$PtI$_2$ (1.62 g, 3.35 mmol), Ag$_2$SO$_4$(1.04 g, 3.69 mmol) and [NP(OCH$_3$)(Glt.K$_2$)]$_n$ (1.0 g, 3.35 mmol) were reacted in accordance with the same procedure as Example 26 to obtain the polymeric platinum complex.

Elemental Analysis (%): C, 15.8; H, 4.78; N, 10.6; P, 6.36; Pt, 35.1

Calculated: C, 15.7; H, 3.97; N, 11.3; P, 6.73; Pt, 36.0

$^1$H NMR(D$_2$O, ppm) 2.2(2H), 2.5(2H), 3.4(3H), 3.8(1H)

IR (KBr cell, cm$^{-1}$) 528(m), 619(m), 889(m), 1112(m), 1245(m), 1337(m), 1389(s), 1621(s), 2948(m), 3241 (s), 3354(s)

EXAMPLE 28

Synthesis of {NP(OC$_2$H$_5$)[Glt.Pt(DACH)]$_{0.8}$(Glt.K$_2$)$_{0.2}$.2H$_2$O}$_n$ Poly(dichlorophosphazene) (3.0 g), L-glutamoyl dibenzyl ester p-toluenesulfonate (13.6 g, 27.2 mmol), ethanol(50 ml), (DACH)PtI$_2$ (1.80 g, 3.19 mmol), Ag$_2$SO$_4$(0.99 g, 3.19 mmol) and [NP(OCH$_2$CH$_3$)(Glt.K$_2$)]$_n$ (1.0 g, 3.19 mmol) were reacted in accordance with the same procedure as Example 26 to obtain the polymeric platinum complex.

Elemental Analysis (%): C, 27.7; H, 5.42; N, 9.01; P, 5.31; Pt, 29.4

Calculated: C, 26.5; H, 4.94; N, 9.44; P, 5.80; Pt, 29.2

$^1$H NMR(D$_2$O, ppm) 1.1–1.3(7H), 1.6(2H), 2.0(4H), 2.4 (4H), 3.4(2H), 3.8(1H)

IR (KBr cell, cm$^{-1}$) 518(m), 874(m), 964(m), 1033(m), 1065(m), 1124(m), 1173(m), 1245(m), 1302(m), 1387(s), 2925(m), 3234(s), 3438(s)

EXAMPLE 29

Synthesis of {NP(NHCH$_3$)[Glt.Pt(DACH)]$_{0.8}$(Glt.K$_2$)$_{0.2}$.2H$_2$O}$_n$ Poly(dichlorophosphazene) (3.0 g), L-glutamoyl dibenzyl ester p-toluenesulfonate (13.6 g, 27.2 mmol), methyl amine (54.4 mmol), (DACH)PtI$_2$ (1.89 g, 3.36 mmol), Ag$_2$SO$_4$ (1.05 g, 3.36 mmol) and [NP(NHCH$_3$)(Glt.K$_2$)]$_n$ (1.0 g, 3.36 mmol) were reacted in accordance with the same procedure as Example 18 to obtain the polymeric platinum complex.

Elemental Analysis (%): C, 25.3; H, 5.53; N, 12.0; P, 5.76; Pt, 30.1

Calculated: C, 25.0; H, 4.90; N, 12.4; P, 5.98; Pt, 30.1

$^1$H NMR(D$_2$O, ppm) 1.1–1.3(4H), 1.6(2H), 2.0(2H), 2.5 (5H), 3.8(1H),

IR (KBr cell, cm$^{-1}$) 518(m), 614(m), 904(m), 1060(m), 1082(m), 1201(m), 1248(m), 1307(m), 1403(s), 2938(m), 3194(s), 3418(s)

EXAMPLE 30

Synthesis of {NP(N(CH$_3$)$_2$[Glt.Pt(DACH)]$_{0.8}$(Glt.K$_2$)$_{0.2}$.2H$_2$O}$_n$ Poly(dichlorophosphazene) (3.0 g), L-glutamoyl dibenzyl ester p-toluenesulfonate (13.6 g, 27.2 mmol), dimethylamine hydrochloride (2.22 g, 27.2 mmol), (DACH)PtI$_2$ (1.81 g, 3.21 mmol), Ag$_2$SO$_4$(1.0 g, 3.21 mmol) and [NP(N(CH$_3$)$_2$(Glt.K$_2$)]$_n$ (1.0 g, 3.21 mmol) were reacted in accordance with the same procedure as Example 29 to obtain the polymeric platinum complex.

Elemental Analysis (%): C, 27.4; H, 5.80; N, 11.8; P, 5.12; Pt, 29.0

Calculated: C, 26.6; H, 5.15; N, 12.1; P, 5.82; Pt, 29.3

$^1$H NMR(D$_2$O, ppm) 1.1–1.3(4H), 1.6(2H), 2.0(4H), 2.4–2.6(10H), 3.8(1H)

IR (KBr cell, cm$^{-1}$) 510(m), 625(m), 980(m), 1056(m), 1151(m), 1162(m), 1240(m), 1293(m), 1397(s), 1628(s), 2923(m), 3198(s), 3432(s)

EXAMPLE 31

Synthesis of {NP(OH)[Am.Pt(DACH)]$_{0.9}$(Am.Na$_2$)$_{0.1}$·2H$_2$O}$_n$

Poly(dichlorophosphazene) (3.0 g), diethylaminomalonate hydrochloride (5.76 g, 27.2 mmol), water(0.49 ml, 27.2 mmol), (DACH)PtI$_2$ (2.50 g, 4.44 mmol), Ag$_2$SO$_4$(1.38 g, 4.44 mmol) and [NP(OH)(Am.Na$_2$)]$_n$ (1.0 g, 4.44 mmol) were reacted in accordance with the same procedure as Example 1 to obtain the polymeric platinum complex.

Elemental Analysis (%): C, 19.4; H, 4.01; N, 9.82; P, 5.88; Pt, 34.5

Calculated: C, 20.3; H, 3.91; N, 10.7; P, 6.23; Pt, 35.3

$^1$H NMR(D$_2$O, ppm) 1.1–1.3(4H), 1.5(2H), 2.0(2H), 2.3(2H), 3.9(1H).

IR (KBr cell, cm$^{-1}$) 503(m), 775(m), 931(m), 1034(m), 1108(m), 1173(m), 1243(m), 1342(s), 1453(m), 1641(s), 2923(m), 3208(s), 3414(s)

EXAMPLE 32

Synthesis of {NP(OH)[Am.Pt(CPA)$_2$]$_{0.9}$(Am.Na$_2$)$_{0.1}$·2H$_2$O}$_n$ (CPA)$_2$PtI$_2$ (2.50 g, 4.44 mmol), Ag$_2$SO$_4$ (1.38 g, 4.44 mmol) and [NP(OH)(Am.Na$_2$)]$_n$ (1.0 g, 4.44 mmol) were reacted in accordance with the same procedure as Example 31 to obtain the title complex.

Elemental Analysis (%): C, 20.8; H, 4.31; N, 10.2; P, 6.23; Pt, 33.9

Calculated: C, 20.3; H, 3.97; N, 10.7; P, 6.23; Pt, 35.3

$^1$H NMR(D$_2$O, ppm) 0.8(8H), 2.3(2H), 3.8(1H)

IR (KBr cell, cm$^{-1}$) 534(m), 754(m), 931(m), 1043(m), 1182(m), 1210(m), 1394(s), 1654(s), 2915(m), 3212(s), 3429(s)

EXAMPLE 33

Synthesis of {NP(OH)[Am.Pt(NH$_3$)$_2$]$_2$]2H$_2$O}$_n$ (NH$_3$)$_2$PtI$_2$ (2.14 g, 4.44 mmol), Ag$_2$SO$_4$(1.38 g, 4.44 mmol) and [NP(OH)(Am.Na$_2$)]$_n$ (1.0 g, 4.44 mmol) were reacted in accordance with the same procedure as Example 31 to obtain the title complex.

Elemental Analysis (%): C, 8.81; H, 3.31; N, 11.9; P, 7.57; Pt, 43.1

Calculated: C, 8.63; H, 2.96; N, 12.6; P, 6.99; Pt, 44.0

$^1$H NMR(D$_2$O, ppm) 3.8(1H)

IR (KBr cell, cm$^{-1}$) 518(m), 619(m), 976(m), 1072(m), 1176(m), 1334(m), 1386(s), 1632(s), 2923(m), 3219(s), 3415(s)

EXAMPLE 34

Synthesis of {NP(OCH$_3$)[Am.Pt(DACH)]$_{0.8}$(Am.Na$_2$)$_{0.2}$·2H$_2$O}$_n$

Poly(dichlorophosphazene) (3.0 g), diethyl aminomalonate hydrochloride (5.76 g, 27.2 mmol), methanol (50 ml), (DACH)PtI$_2$ (2.35 g, 4.18 mmol), Ag$_2$SO$_4$ (1.30 g, 4.18 mmol) and [NP(OCH$_3$)(Am.Na$_2$)]$_n$ (1.0 g, 4.18 mmol) were reacted in accordance with the same procedure as Example 13 to obtain the polymeric platinum complex.

Elemental Analysis (%): C, 21.5; H, 4.31; N, 9.72; P, 5.90; Pt, 31.6

Calculated: C, 21.8; H, 4.20; N, 10.4; P, 6.39; Pt, 32.2

$^1$H NMR(D$_2$O, ppm) 1.1–1.3(4H), 1.5(2H), 2.0(2H), 2.3(2H), 3.4(3H), 3.8(1H)

IR (KBr cell, cm$^{-1}$) 507(m), 775(m), 931(m), 1071(m), 1033(m), 1162(m), 1248(m), 1323(s), 1651(s), 2930(m), 3202(s), 3428(s)

EXAMPLE 35

Synthesis of {NP(OCH$_3$)[Am.Pt(NH$_3$)$_2$]$_{0.85}$(Am.Na$_2$)$_{0.15}$·2H$_2$O}$_n$ (NH$_3$)$_2$PtI$_2$ (2.02 g, 4.18 mmol), Ag$_2$SO$_4$(1.30 g, 4.18 mmol) and [NP(OCH$_3$)(Am.Na$_2$)]$_n$ (1.0 g, 4.18 mmol) were reacted in accordance with the same procedure as Example 26 to obtain the title complex.

Elemental Analysis (%): C, 12.0; H, 3.81; N, 11.5; P, 6.69; Pt, 37.9

Calculated: C, 11.2; H, 3.33; N, 12.1; P, 7.25; Pt, 38.8

$^1$H NMR(D$_2$O, ppm) 3.3(3H), 3.8(1H)

IR (KBr cell, cm$^{-1}$) 507(m), 614(m), 714(m), 920(m), 1032(m), 1074(m), 1186(m), 1234(m), 1387(s), 1443(m), 1636(s), 2932(m), 3251(s), 3421(s)

EXAMPLE 36

Synthesis of {NP(NHCH$_3$)[Am.Pt(DACH)]$_{0.8}$(Am.Na$_2$)$_{0.2}$·2H$_2$O}$_n$

Poly(dichlorophosphazene) (3.0 g), diethyl aminomalonate hydrochloride (5.76 g, 27.2 mmol), methylene (54.4 ml), (DACH)PtI$_2$ (2.36 g, 4.20 mmol), Ag$_2$SO$_4$ (1.31 g, 4.20 mmol) and [NP(NHCH$_3$)(Am.Na$_2$)]$_n$ (1.0 g, 4.20 mmol) were reacted in accordance with the same procedure as Example 18 to obtain the polymeric platinum complex.

Elemental Analysis (%): C, 23.1; H, 4.31; N, 12.6; P, 5.83; Pt, 31.9

Calculated: C, 21.8; H, 4.42; N, 13.3; P, 6.40; Pt, 32.3

$^1$H NMR(D$_2$O, ppm) 1.1–1.3(4H), 1.5(2H), 2.0(2H), 2.3(2H), 2.6(3H), 3.8(1H)

IR (KBr cell, cm$^{-1}$) 518(m), 609(m), 765(m), 1119(m), 1259(m), 1318(m), 1323(s), 1447(m), 1661(m), 2912(m), 3224(s), 3396(s)

Anticancer activity

Assays to evaluate the anticancer activity of the present polymeric platinum complexes were performed according to a standard method [Goldin et al., Europ. J. Cancer, 17, 129(1981)].

Mouse leukenua cells L1210 cells (10$^6$ cells/mouse) were transplanted to each six to eight-week-old BDFI mouse (eight animals for 1 group), and a solution of the platinum complex according to the present invention dissolved in 0.9% physiological saline was then administered at doses of 30–60 mg/kg by intra peritoneal injection at 1st, 5th and 9th day. Mean value of the increased life span (ILS, %) and number of the animals survived after 60 days were examined. For comparison, cisplatin and carboplatin were used.

The results are shown in Table 1. It is found that the anticancer activity of the complexes of the present invention is much higher than that of cisplatin or carboplatin.

In addition, acute toxicity of some representative complexes of the present invention ($LD_{50}$=160 mg/kg in Example 1; $LD_{50}$=130 mg/kg in Example 21) is much lower than that of cisplatin ($LD_{50}$=13 mg/kg) and comparative to that of carboplatin ($LD_{50}$=180 mg/kg). Thus, the complexes of the present invention are highly promising to be developed as the third-generation anticancer agent.

TABLE 1

| Compound | Dose (mg/kg) | ILS (%) | No. of survived animals after 60 days |
| --- | --- | --- | --- |
| Example 1 | 60 | >542 | 8/8 |
|  | 30 | >288 | 3/8 |
| Example 11 | 30 | >279 | 3/8 |
| Example 12 | 30 | >460 | 6/8 |
| Example 13 | 30 | >142 | 1/8 |
| Example 15 | 30 | >143 | 1/8 |
| Example 17 | 30 | >385 | 5/8 |
| Example 18 | 30 | >195 | 1/8 |
| Example 20 | 30 | 103 | 0 |
| Example 21 | 60 | >435 | 6/8 |
|  | 30 | >157 | 1/8 |
| Example 36 | 30 | 123 | 0 |
| Cisplatin | 4 | 80 | 0 |
| Carboplatin | 40 | 60 | 0 |

What is claimed is:

1. A polymeric platinum complex represented by following formula (I):

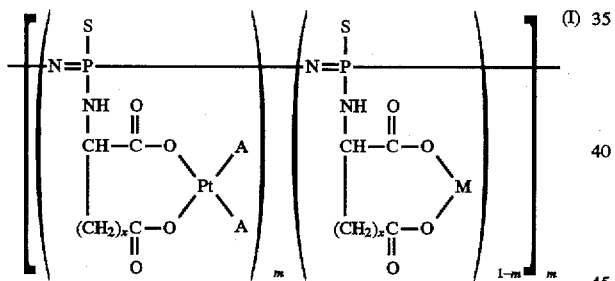

wherein, polymeric backbone is a polyphosphazene having P=N repeating unit; S represents hydroxy group, alkoxy group such as methoxy, ethoxy or (2-methoxy)ethoxy group, or alkylamine group such as methylamine or dimethylamine group as solubilizing group and S is attached to the phosphorus on the polymeric backbone through an oxygen or nitrogen atom: A represents ammonia, or $C_1$–$C_3$ alkylamine such as methylamine, ethylamine or cyclopropylamine as monodentate neutral ligand, or AA-type bidentate chelate amine selected from the group consisting of ethylenediamine, propylenediamine, 2-hydroxy-1,3-diaminopropane, 2,2-dimethyl-1,3-diaminopropane, 1,1-diaminomethylcyclobutane, tetrahydro-4H-pyrane-4,4-dimethanamine, 2,2-bisaminomethyl-1,3-propandio and trans(±)-1,2-diaminocyclohexane; x designating the type of dicarboxylic amino acid as ion group represents 0, 1 or 2, M designates two sodium or potassium ions or alkaline metal ions or one calcium or barium ion or one alkaline earth metal ion; m is 0.2 to 1; and n is 10 to 100.

2. A polymeric platinum complex according to claim 1, wherein m is 1.

3. A process for the preparation of a polymeric platinum complex of the formula

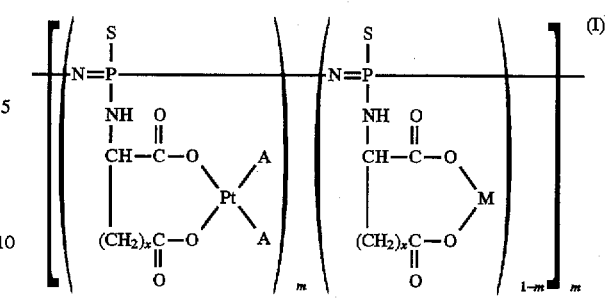

comprising:

(a) mixing poly(dichlorophosphazene) in a solvent selected from the group consisting of benzene, toluene, tetrahydrofuran and dioxane with sufficient amounts of a dicarboxylic amino acid selected from the group consisting of derivatives of aminomalonic acid, aspartic acid and glutamic acid and a solubilizing agent having the formula SH to form a polymeric precipitate;

(b) hydrolyzing the product of (a) with alkaline metal hydroxide or alkaline earth metal hydroxide and mixing the resulting mixture at room temperature for sufficient time to produce an alkaline metal salt of formula (II) or alkaline earth metal salt of formula (III)

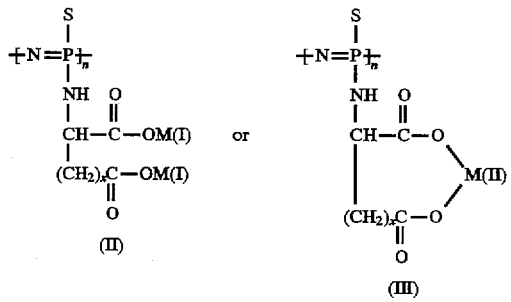

respectively;

(c) reacting the product of (b) with a diamine platinum (II) salt of formula (IV)

in a molar ratio of 1:0.2 to 1:1, in an aqueous solution at room temperature to obtain the polymeric complex of Formula I:

wherein the polymeric backbone is a polyphosphazene having P=N repeating unit;

S is hydroxy, alkoxy or alkylamine, and S is attached to the phosphorous on the polymeric backbone through an oxygen or nitrogen atom;

A is ammonia or $C_1$–$C_3$ alkylamine or A when taken together with the other A forms a AA type bidentate chelate amine selected from the group consisting of ethlyenediamine, propylenediamine, 2-hydroxy-1,3-diaminopropane, 2,2-dimethyl-1,3-diaminopropane, 1,1-diaminomethylcyclobutane, tetrahydro-4H-pyrane-4,4-dimethanamine, 2,2-bis-aminomethyl-1, 3-propandiol and trans(±)-1,2-diaminocyclohexane;

x is 0, 1 or 2;

M is two alkaline metal ions or two ammonium or one alkaline earth ion;

m is 0.2 to 1;

n is 10–100;
M (I) is alkaline earth metal or ammonium;
M (II) is an alkaline earth metal ion; and
$X_2$ is an anion.

4. The platinum complex of claim 1 which is

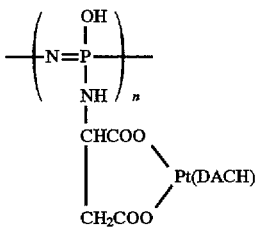

wherein DACH is trans(±)-1,2-diaminocyclohexane.

5. The platinum complex of claim 1 which is

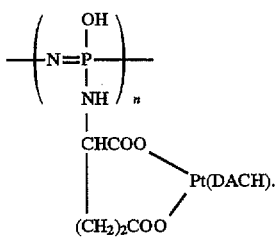

wherein DACH is trans(±)-1,2-diaminocyclohexane.

6. An anticancer composition comprising as the active component an anti-cancer effective amount of the platinum complex according to claim 1 or claim 2.

7. The anti-cancer composition according to claim 6 wherein the platinum complex is associated with physiological saline.

8. The anti-cancer composition according to claim 6 in which the complex is dissolved in solution suitable for therapeutic administration.

9. A method of treating an animal with a cancer susceptible to platinum therapy which comprises administering to said animal in need of such treatment an anti-cancer effective amount of a polymeric platinum complex of claim 1 or 2.

10. A process according to claim 3, wherein alkaline metal salt of general formula (II) or alkaline earth metal salt of general formula (III) is reacted with diamineplatinum (II) salt of general formula (IV) in a molar ratio of 1:1.

11. A process according to claim 3, wherein dicarboxylic amino acid is selected form the group consisting of methyl ester, ethyl ester, benzyl ester and alkylamide of aminomalonic acid, aspartic acid or glutamic acid, and the S is selected from the group consisting of hydroxy group, alkoxy group selected from methoxy group, ethoxy group or (2-methoxy)ethoxy group, or water soluble amine selected from methylene or dimethylamine.

12. A process according to claim 3, wherein the alkaline metal is sodium or potassium, the alkaline earth metal is barium or calcium, and the diamineplatinum (II) salt of general formula (IV) is diamineplatinum (II) sulfate or dimeplatinum (II) nitrate.

13. A process according to claim 3, wherein alkaline metal salt of general formula (II) and diamineplatinum (II) sulfate or diamineplatinum (II) nitrate of general formula (IV) are reacted in an aqueous solution at room temperature in a molar ratio of 1:0.2 to 1:1; the reaction mixture is concentrated; and then organic solvent is added thereto.

14. A process according to claim 13, wherein the organic solvent is a single solvent or a mixed solvent selected from acetone, ethanol, methanol and ethyl ether.

15. A process according to claim 3, wherein alkaline metal salt of general formula (II) and diamineplatinum (II) nitrate of general formula (IV) are reacted in an aqueous solution at room temperature in a molar ratio of 1:0.2 to 1:1; and then further comprising dialyzing the product of step (c) using a semipermeable membrane which transits molecules of molecular weight 1000 or less thereby removing by product.

16. A process according to claim 12, calcium or barium salt of formula (III) and diamineplatinum (II) sulfate of formula(IV) are reacted in an aqueous solution at room temperature in a molar ratio of 1:0.2 to 1:1, and precipitated calcium or barium sulfate is removed by precipitation.

* * * * *

UNITED STATES PATENT AND TRADEMARK OFFICE
CERTIFICATE OF CORRECTION

PATENT NO. : 5,665,343

DATED : September 9, 1997

INVENTOR(S) : Youn Soo Sohn, et al.

It is certified that error appears in the above-identified patent and that said Letters Patent is hereby corrected as shown below:

In the Abstract, at the right end of the formula (I): "m" should read --n--

Column 2, line 42, at the right end of the formula (I): "m" should read --n--

Column 3, line 10: "(I)" should read --(II)--

Column 3, line 11: "(I)" should read --(III)--

Column 3, line 56: "600" should read --60--

Column 4, line 66: "polyphohphazene" should read --polyphosphazene--

Column 5, line 54: "m=10" should read --n=10--

Column 6, line 5: "(dichlomphosphazene)" should read --(dichlorophosphazene)--

Column 11, line 62: "C,4.3" should read --C,24.3--

UNITED STATES PATENT AND TRADEMARK OFFICE
CERTIFICATE OF CORRECTION

PATENT NO. : 5,665,343

DATED : September 9, 1997

INVENTOR(S) : Youn Soo Sohn, et al.

It is certified that error appears in the above-identified patent and that said Letters Patent is hereby corrected as shown below:

Column 15, line 65: "$cm^{31\ 1}$" should read --$CM^{-1}$--

Column 16, line 63: "leukenua" should read --leukemia--

Column 16, line 63: after "L1210" delete --cells--

Column 17, line 45, Claim 1, at the right end of the Formula (I): "m" should read --n--

Column 18, line 11, Claim 3, at the right end of the Formula (I): "m" should read --n--

Column 20, line 8, Claim 11: "form" should read --from--

Column 20, line 36, Claim 16: "claim 12," should read --claim 12, wherein--

Signed and Sealed this

Tenth Day of August, 1999

Attest:

Q. TODD DICKINSON

Attesting Officer    Acting Commissioner of Patents and Trademarks